(12) United States Patent
Dicesare et al.

(10) Patent No.: US 8,221,441 B2
(45) Date of Patent: Jul. 17, 2012

(54) ROTARY-ACTUATED MEDICAL PUNCTURING DEVICE

(75) Inventors: Paul Dicesare, Easton, CT (US); Christopher Battles, Seymour, CT (US); Jeffrey Radziunas, Wallingford, CT (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 454 days.

(21) Appl. No.: 11/568,619

(22) PCT Filed: May 4, 2005

(86) PCT No.: PCT/US2005/015578
§ 371 (c)(1),
(2), (4) Date: Jan. 17, 2008

(87) PCT Pub. No.: WO2005/110226
PCT Pub. Date: Nov. 24, 2005

(65) Prior Publication Data
US 2009/0118753 A1    May 7, 2009

Related U.S. Application Data

(60) Provisional application No. 60/569,479, filed on May 7, 2004.

(51) Int. Cl.
*A61B 17/14* (2006.01)
(52) U.S. Cl. ..................................................... 606/182
(58) Field of Classification Search .................. 606/180, 606/181, 182, 184, 185, 167; 600/583; 604/136, 604/137, 138, 139
See application file for complete search history.

(56) References Cited

U.S. PATENT DOCUMENTS

| | | | |
|---|---|---|---|
| 4,416,279 | A | 11/1983 | Lindner et al. |
| 4,817,603 | A | 4/1989 | Turner et al. |
| 4,869,249 | A | 9/1989 | Crossman et al. |
| 5,366,470 | A | 11/1994 | Ramel |
| 5,540,709 | A | 7/1996 | Ramel |
| 5,755,733 | A | 5/1998 | Morita |
| 5,951,582 | A | 9/1999 | Thorne et al. |
| 6,248,120 | B1 | 6/2001 | Wyszogrodzki |
| 6,419,661 | B1 | 7/2002 | Kuhr et al. |
| 6,432,120 | B1 | 8/2002 | Teo |

(Continued)

FOREIGN PATENT DOCUMENTS

JP    7-500995  T    2/1995

(Continued)

*Primary Examiner* — Ryan Severson
*Assistant Examiner* — Jonathan W Miles
(74) *Attorney, Agent, or Firm* — The Webb Law Firm (57) ABSTRACT

The medical puncturing device includes an actuator, a shield, and a skin puncturing assembly. The actuator and shield are movable relative to one another. The skin-puncturing assembly includes a carrier and a skin-puncturing element. A distal end of the skin puncturing element is adapted for puncturing the skin of a patient. The carrier is movable from a retracted position wherein the distal end of the skin-puncturing element is disposed within the shield to a puncturing position wherein the distal end of the skin-puncturing element is exposed to puncture the skin of a patient. The carrier is maintained in the retracted position by interference engagement between the carrier and shield. A drive spring is provided to move the carrier from the retracted to puncturing positions. A retraction spring is provided to return the carrier to a position wherein the shield encompasses the skin puncturing element.

20 Claims, 10 Drawing Sheets

U.S. PATENT DOCUMENTS

| | | |
|---|---|---|
| 7,077,828 B2 | 7/2006 | Kuhr et al. |
| 7,238,192 B2 * | 7/2007 | List et al. ................ 606/182 |
| 7,322,998 B2 | 1/2008 | Kuhr et al. |
| 2002/0169470 A1 | 11/2002 | Kuhr et al. |
| 2003/0216767 A1 * | 11/2003 | List et al. ................ 606/181 |

FOREIGN PATENT DOCUMENTS

| | | |
|---|---|---|
| WO | 9309723 | 5/1993 |

* cited by examiner

ROTARY-ACTUATED MEDICAL PUNCTURING DEVICE

The present application claims the benefit of U.S. Provisional Application No. 60/569,479, filed on May 7, 2004, under 35 U.S.C. 119(e).

BACKGROUND OF THE INVENTION

1. Field of the Invention present invention relates generally to medical puncturing devices, commonly referred to as lancets, used to take blood samples from patients and, more specifically, to a medical puncturing device that ensures sterility before use and safe and secure disposal after use.

2. Description of Related Art

Medical puncturing devices are used in the medical field for puncturing the skin of a patient to obtain a capillary blood sample from the patient. Certain diseases, such as diabetes, require that the patient's blood be tested on a regular basis to monitor, for example, the patient's blood sugar levels. Additionally, test kits, such as cholesterol test kits, often require a blood sample for analysis. The blood collection procedure usually involves pricking a finger or other suitable body part in order to obtain the blood sample. Typically, the amount of blood needed for such tests is relatively small and a small puncture wound or incision normally provides a sufficient amount of blood for these tests.

Various medical puncturing devices are commercially available to hospitals, clinics, doctors' offices, and the like, as well as to individual consumers. Such devices typically include a sharp-pointed member such as a needle, or a sharp-edged member such as blade, that is used to make a quick puncture wound or incision in the patient's skin in order to provide a small outflow of blood. It is often physiologically and psychologically difficult for many people to prick their own finger with a hand-held needle or blade. As a result, medical puncturing devices have evolved into automatic devices that puncture or cut the skin of the patient upon the actuation of a triggering mechanism. In some devices, the needle or blade is kept in a standby position until it is triggered by the user, who may be a medical professional in charge of drawing blood from the patient, or the patient himself or herself. Upon triggering, the needle or blade punctures or cuts the skin of the patient, for example on the finger. Often, a spring is incorporated into the device to provide the "automatic" force necessary to puncture or cut the skin of the patient.

It is of the utmost importance in the medical field that such medical puncturing devices or lancets are in a sterile condition before use. Today, generally without exception, medical puncturing devices or lancets are manufactured and packaged in a sterilized condition before they are distributed to medical professionals and members of the public who have a need for such devices. The sterile packaging maintains the sterility of the device, ensuring that the surrounding environment does not contaminate it until use. In addition, it is also of increasing importance that the user or another person does not come into contact with the needle or blade after use of the device. With the concern over blood-borne diseases, medical professionals are required to take great care with medical devices that come into contact with the blood of patients. Thus, an important aspect of medical puncturing device/lancet design is concerned with preventing the needle or blade of the device from wounding the user or another person after the blood sample is drawn from the patient. Once used, the needle or blade should be shielded to prevent the needle or blade from wounding the user or another person handling the device. Moreover, the medical puncturing device or lancet should be disposable to eliminate the chances of disease transmission due to the needle or blade being used on more than one person. In this regard, the medical puncturing device or lancet should ideally be designed for one firing, and have safety features to prevent reuse.

Advances have been made in recent years to increase safety in operating and handling used medical puncturing devices. For example, medical puncturing devices are currently available which are single shot devices that feature automatic ejection and retraction of the puncturing or cutting element from and into the device. Examples of such medical puncturing devices are disclosed in U.S. Pat. Nos. 6,432,120; 6,248,120; 5,755,733; and 5,540,709.

U.S. Pat. No. 6,432,120 to Teo discloses a lancet assembly that includes a lancet holder, which contains a spring-loaded lancet structure. The spring-loaded lancet structure includes a single spring that effects the ejection and retraction of a lancet needle upon the triggering of the structure. U.S. Pat. No. 6,248,120 to Wyszogrodzki discloses a puncturing device comprised of a housing, shielding portion, a piston with a puncturing tip, and drive and return springs that eject and retract the piston, respectively, upon the breakage of internal wing elements in the housing. U.S. Pat. No. 5,755,733 to Morita discloses a lancet assembly that includes a combined holder and lancet structure. The lancet structure includes a lancet member with a puncturing tip and a compressible spring member that causes the lancet member to puncture the skin of a patient upon actuation of a pair of actuating arms.

U.S. Pat. No. 5,540,709 to Ramel discloses a lancet device that includes a housing enclosing a slidable trigger, which is used to trigger a compressed spring that powers a piercing lancet member to pierce the skin of a patient. The housing includes a pair of internal fingers that engage the body of the lancet member, which are then released of engagement with the lancet member body by axial force applied by the user to the slidable trigger. Other medical puncturing devices or lancets known in the art are disclosed in U.S. Pat. Nos. 4,869,249 and 4,817,603. The devices disclosed in these references include a cap that is used to protect a needle or to keep the needle sterile.

SUMMARY OF THE INVENTION

In view of the foregoing, a need generally exists in the medical field for a medical puncturing device that ensures sterility before use and safe and secure disposal after use. Additionally, a need exists in the medical field for a simple, inexpensive, reliable, self-activating, and disposable medical puncturing device for use in collecting blood samples. Moreover, there is a need for a medical puncturing device in which production of puncture wounds and/or incisions is consistent and well-controlled. The foregoing needs are fulfilled with a medical puncturing device in accordance with the embodiments of the present invention. The medical puncturing device generally includes an actuator having at least one release element extending therefrom, a shield and a skin puncturing assembly. The shield and the actuator are movably associated with each other. The skin puncturing assembly disposed at least partially within the shield and comprising a carrier and a skin puncturing element mounted to the carrier, a distal end of the skin puncturing element adapted for puncturing the skin of a patient, the carrier movable from a first position to a second position. The release element is configured such that relative movement between the actuator and shield causes the at least one release element to engage the carrier and align at least one tab provided on one of the carrier and shield with at least one slot formed in the other of the carrier and shield, enabling the carrier to move from the first position to the second position.

In accordance with another embodiment of the invention, a method of actuating a medical puncturing device is also provided. The method comprises providing the medical puncturing device comprising an actuator, a shield, and a skin puncturing assembly disposed at least partially within the shield and comprising a movable carrier and a skin puncturing element mounted to the carrier. A distal end of the skin puncturing element is adapted for puncturing the skin of a patient. The actuator and shield movably associated with each other, and the actuator has at least one release element extending therefrom. The method further includes causing relative movement between the actuator and shield, such that the release element engages and moves the carrier until at least one tab provided on one of the carrier and shield aligns with at least one slot formed in the other of the carrier and shield, enabling the carrier to move from a retracted position wherein the distal end of the skin puncturing element is disposed within the shield to a puncturing position wherein the distal end of the skin puncturing element is exposed from the shield to puncture the skin of a patient.

In accordance with a further embodiment of the invention, a method of assembling a medical puncturing device is also provided. The method includes providing an actuator having an open proximal end and an open distal end, inserting a shield into the actuator proximal end, a distal end of the shield extending outward from the actuator distal end and inserting a skin puncturing assembly into the actuator proximal end, the skin puncturing assembly comprising a movable carrier and a skin puncturing element mounted to the carrier, the skin puncturing element having a distal end adapted for puncturing the skin of a patient. The method further includes positioning a drive spring in the actuator and at least partially about the carrier, wherein the drive spring is adapted to move the carrier from a retracted position, and wherein the distal end of the skin puncturing element is disposed within the shield to a puncturing position wherein the distal end of the skin puncturing element is exposed from the shield distal end for puncturing the skin of a patient. The skin puncturing assembly is then inserted into the actuator such that at least one tab provided on one of the carrier and shield engages at least at least one edge on the other of the carrier and shield and is misaligned from the at least one slot, preventing the carrier from moving from the retracted to puncturing positions.

In accordance with another embodiment of the invention, a method of actuating a medical puncturing device is provided. The method includes providing the medical puncturing device comprising an actuator, a shield, and a skin puncturing assembly disposed at least partially within the shield, the skin puncturing assembly comprising a movable carrier and a skin puncturing element mounted to the carrier, the skin puncturing element having a distal end adapted for puncturing the skin of a patient, and the actuator and shield movably associated with each other. The method further includes causing relative movement between the actuator and shield, such that the actuator engages the carrier and rotates the carrier from an interference engagement with the shield to a position allowing the skin puncturing assembly to move axially within the shield to a position exposing the distal end of the skin puncturing element for puncturing the skin of the patient.

In still another embodiment of the invention, a medical puncturing device is provided comprising an actuator and a shield, the shield and the actuator movably associated with each other. The medical puncturing device further includes a skin puncturing assembly disposed at least partially within the shield, the skin puncturing assembly comprising a carrier and a skin puncturing element mounted to the carrier, and the carrier movable from a first position to a second position. When the carrier is in the first position, the shield has a shield interference surface engageable with a carrier interference surface of the carrier. In addition, when a force is applied to the actuator, the carrier is capable of rotation which enables disengagement of the shield interference surface from the carrier interference surface, thereby causing the carrier to move from the first position to the second position.

In yet another embodiment of the invention, a medical puncturing device is provided comprising an actuator having a proximal end and a distal end, a shield having a proximal end and a distal end, the shield proximal end movably associated with the actuator distal end, and a skin puncturing assembly disposed at least partially within the shield and comprising a carrier and a skin puncturing element mounted to the carrier. A distal end of the skin puncturing element is adapted for puncturing the skin of a patient. The carrier is movable from a retracted position wherein the distal end of the skin puncturing element is disposed within the shield to a puncturing position wherein the distal end of the skin puncturing element is exposed from the distal end of the shield to puncture the skin of the patient. The carrier comprises at least one tab. Relative axial movement between the actuator and shield causes rotation of a release element disposed within the actuator and operatively associated with the carrier. The release assembly is adapted to maintain the carrier in the retracted position until the axial movement between the actuator and shield and enable the carrier to move from the retracted position to the puncturing position upon the axial movement between the actuator and shield.

In another embodiment of the invention, a method of actuating a medical puncturing device is provided. The medical puncturing device comprises an actuator, a shield, and a skin puncturing assembly disposed at least partially within the shield. The skin puncturing assembly comprises a movable carrier and a skin puncturing element mounted to the carrier, the skin puncturing element having a distal end adapted for puncturing the skin of a patient, and the actuator and shield movably associated with each other. Relative axial movement is caused between the actuator and shield, such that the actuator rotates a release element associated with the carrier to a position allowing the carrier to move axially within the shield to a position exposing the distal end of the skin puncturing element for puncturing the skin of the patient.

DETAILED DESCRIPTION OF THE INVENTION

For purposes of the description hereinafter, the terms "upper", "lower", "right", "left", "vertical", "horizontal", "top", "bottom", and derivatives thereof shall relate to embodiments of the invention, as it is oriented in the drawing figures. However, it is to be understood that embodiments of the invention may include many alternative variations and step sequences except where expressly specified to the contrary. It is also to be understood that the specific devices and processes illustrated in the attached drawings and described in the following text are simply exemplary embodiments of the invention. Hence, specific dimensions and other physical characteristics related to the embodiments disclosed hereinafter are not to be considered limiting.

Referring to FIGS. 1-5, a medical puncturing device or lancet 10 (hereinafter "puncturing device 10") in accordance with an embodiment of the present invention is generally illustrated. The puncturing device 10 generally includes an actuator 12, a shield 13 movably associated with the actuator, and a skin puncturing assembly 14 disposed within the actuator 12 and shield 13. The actuator 12 and shield 13 are movably associated with each other to permit relative movement therebetween. Preferably, the shield 13 is axially movable relative to the actuator 12, such that the shield 13 may be moved proximally into the actuator 12 during operation of the puncturing device 10.

The actuator 12 has a generally tubular structure having a distal end 16 and a proximal end 18. The actuator 12 is preferably open-ended at the distal and proximal ends 16, 18. An end cap 20 may be provided at the proximal end 16 of the actuator 12, closing the proximal end 18 of the actuator 12 and forming the proximal end 18 of the actuator 12. Alternatively, the actuator 12 may be formed to have a closed proximal end 18 instead of the end cap 20. The closed proximal end 18 of the actuator 12 would be integrally formed with the remainder of the body of the actuator 12 in this variation of the puncturing device 10.

Figure 3:
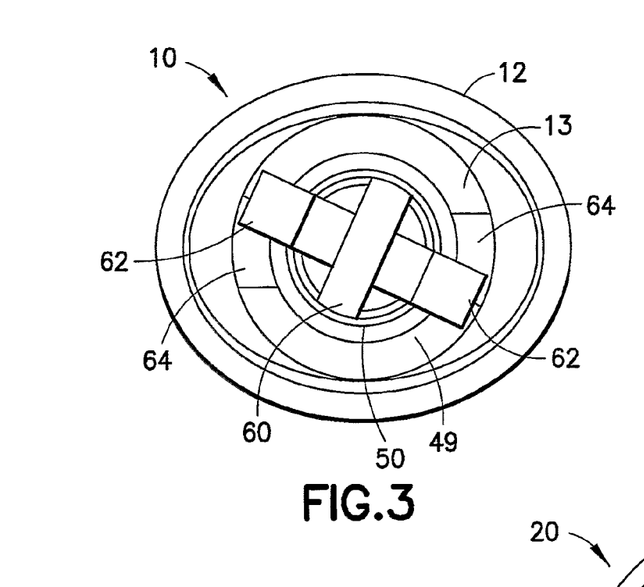
FIG. 3 is an end view of the medical puncturing device of FIG. 1, with an end cap used to close a proximal end of an actuator of the medical puncturing device removed for viewing the interior of the medical puncturing device.
Figure 4:
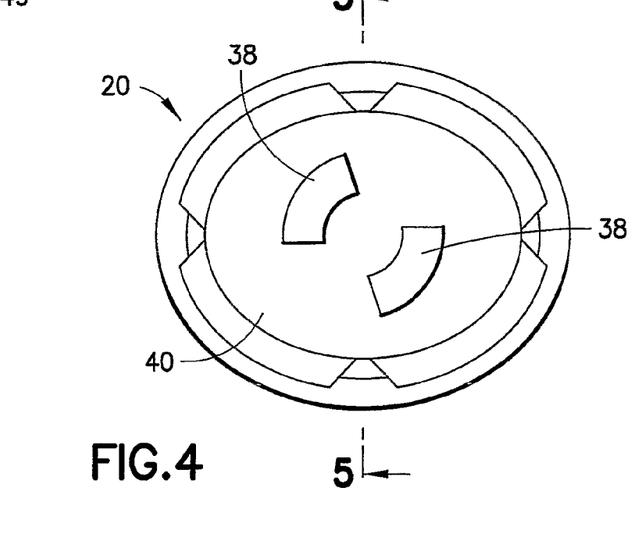
FIG. 4 is an interior end view of the end cap used in the medical puncturing device of FIG. 1.
Figure 5:
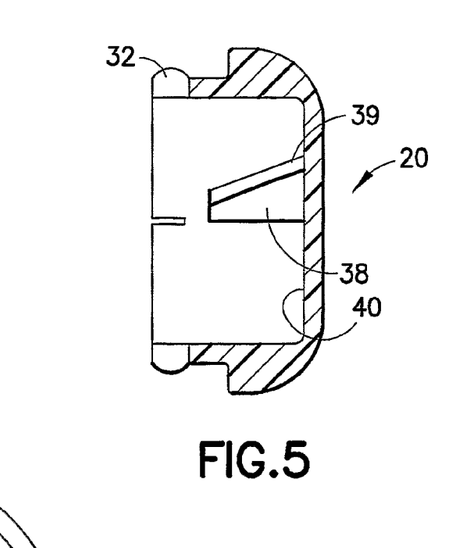
FIG. 5 is cross-sectional view taken along line 5-5 in FIG. 4.

The actuator 12 may be made of a substantially rigid material such as a hard plastic, preferably a medical-grade plastic. The end cap 20 may also be made of a similar material to the actuator 12. The actuator 12 may have any suitable cross-sectional shape, such as oval, circular, or polygonal. However, because the actuator 12 is intended to be grasped between the fingertips of the user of the puncturing device 10, the cross-sectional shape of the actuator 12 is preferably selected so that the actuator 12 is easily manipulated by the user's fingertips. An oval or circular cross-sectional shape for the actuator 12 best fits this requirement and is presently preferred, as depicted in FIG. 3. The shield 13 preferably has a cross-sectional shape that corresponds to the actuator 12, and may be circular, oval, or polygonal in transverse cross-section in a similar manner to the actuator 12.

Figure 1:
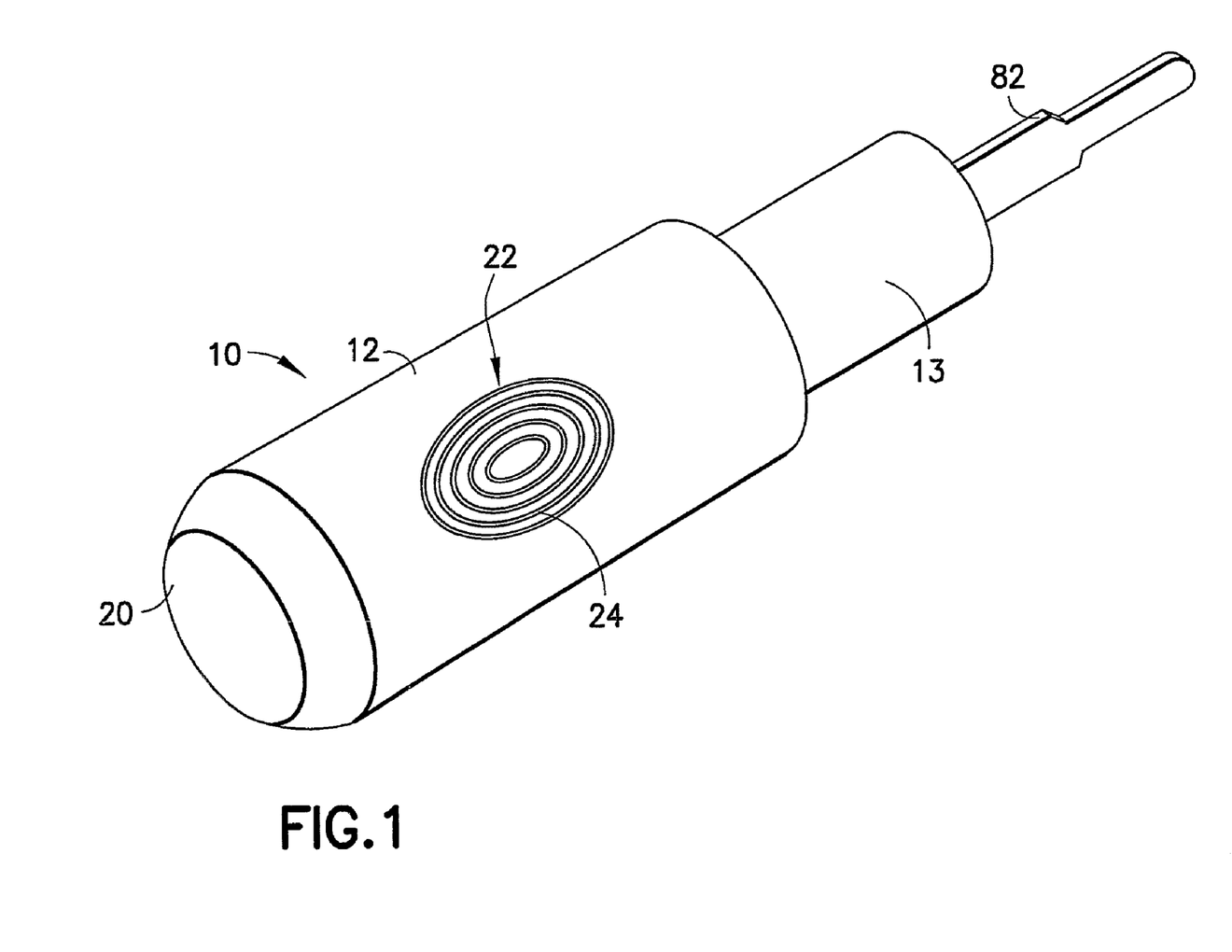
FIG. 1 is a perspective view of a medical puncturing device in accordance with an embodiment of the present invention, showing the device with a removable tip guard.

Additionally, the actuator 12 may be formed with finger pads 22 provided on opposing sides of the actuator 12 for grasping by the user of the puncturing device 10. One of the finger pads 22 is illustrated in FIG. 1 and is formed by concentric oval rings 24 that are raised from an outer or external surface 26 of the actuator 12. The finger pads 22 provide gripping surfaces for the user of the puncturing device 10, and also provide a tactile indication of where the user of the puncturing device 10 should place his or her fingertips when actuating the puncturing device 10 in the manner described herein.

The actuator 12 has a generally uniform wall thickness over its length up to a distal portion 28 of the actuator 12, where the wall thickness of the actuator 12 increases. The increased wall thickness of the distal portion 28 of the actuator 12 forms an internal edge 30, preferably a circumferentially-extending internal edge 30, within the actuator 12 that limits the axial distal movement of the shield 13 relative to the actuator 12 as discussed herein. The increased wall thickness at the distal portion 28 of the actuator 12 extends or forms approximately 10-40% of the length of the actuator 12 and further forms the distal end 16 of the actuator 12.

The end cap 20, if present, may be engaged with the actuator 12 by a frictional, snap-fit type of engagement. Once engaged with the actuator 12, the frictional engagement between the end cap 20 and actuator 12 is preferably of sufficient strength to prevent the end cap 20 from being removed easily from the actuator 12 to reduce the ability of a user of the puncturing device 10 to tamper with the puncturing device 10 after manufacturing. In particular, the end cap 20 includes a circumferential detent 32 that cooperates with a circumferential recess 34 formed in an internal or interior surface 36 of the actuator 12. To further secure the connection between the end cap 20 and actuator 12, a medical-grade adhesive may be provided in the recess 34 during the manufacturing process for the puncturing device 10, thereby adhesively securing the detent 32 in the recess 34.

The end cap 20 further includes at least one and preferably a pair of release elements 38 extending distally from the actuator 12, and internally within the actuator 12. The release elements 38 define respective cam surfaces or edges 39, which are used to actuate the puncturing device 10. The release elements 38 act as cam elements or members for actuating the puncturing device 10, as discussed herein. The release elements 38 extend from an inner side 40 of the end cap 12. The cam surfaces or edges 39 are preferably arcuate-shaped (i.e., curved) for activating the actuating device 10. If the proximal end 18 of the actuator 12 is formed by the body of the actuator 12, the release elements 38 will extend from an internal or inner side of the actuator proximal end 18 in accordance with an embodiment of the present invention. The release elements 38 are preferably integrally formed with the end cap 20, as illustrated in FIG. 2, or the actuator proximal end 18 as desired.

The shield 13 includes a distal end 42 and a proximal end 44. The shield 13 is disposed partially within the actuator 12, and is axially movable relative to the actuator 12. In particular, the proximal end 44 of the shield 13 is disposed within the actuator 12, at the distal end 16 of the actuator 12. As shown in FIG. 2, the distal end 42 of the shield 13 is preferably formed with an internally-extending portion 46. The internally-extending portion 46 defines a recess or pocket 48 for housing a spring or other biasing element, as discussed further herein.

The shield 13 further includes a proximal portion 49 formed at the proximal end 40 of the shield 13. The proximal portion 49 generally cooperates or engages with the internal surface 36 of the actuator 12, but enables axial movement between the shield 13 and the actuator 12. The proximal portion 49 is formed by an area of increased wall thickness on the body of the shield 13, and defines a raised area or lip generally adapted to engage or contact the internal edge 30 formed by the distal portion 28 of the actuator 12. The interference engagement of the proximal portion 49 with the internal edge 30 limits the ultimate axial distance the shield 13 may move relative to the actuator 12, and further prevents the shield 13 from being removed from the distal end 16 of the actuator 12 once inserted therein during manufacturing. The interference engagement of the proximal portion 49 with the internal edge 30 thus minimizes the ability of a user of the puncturing device 10 to tamper with the puncturing device 10 after manufacturing. The proximal portion 49 preferably extends circumferentially around the body of the shield 13, and may further be used to guide the movement of the shield 13 proximally into the actuator 12, and thereby function as a guiding element for the shield 13 relative to the actuator 12.

Figure 2:
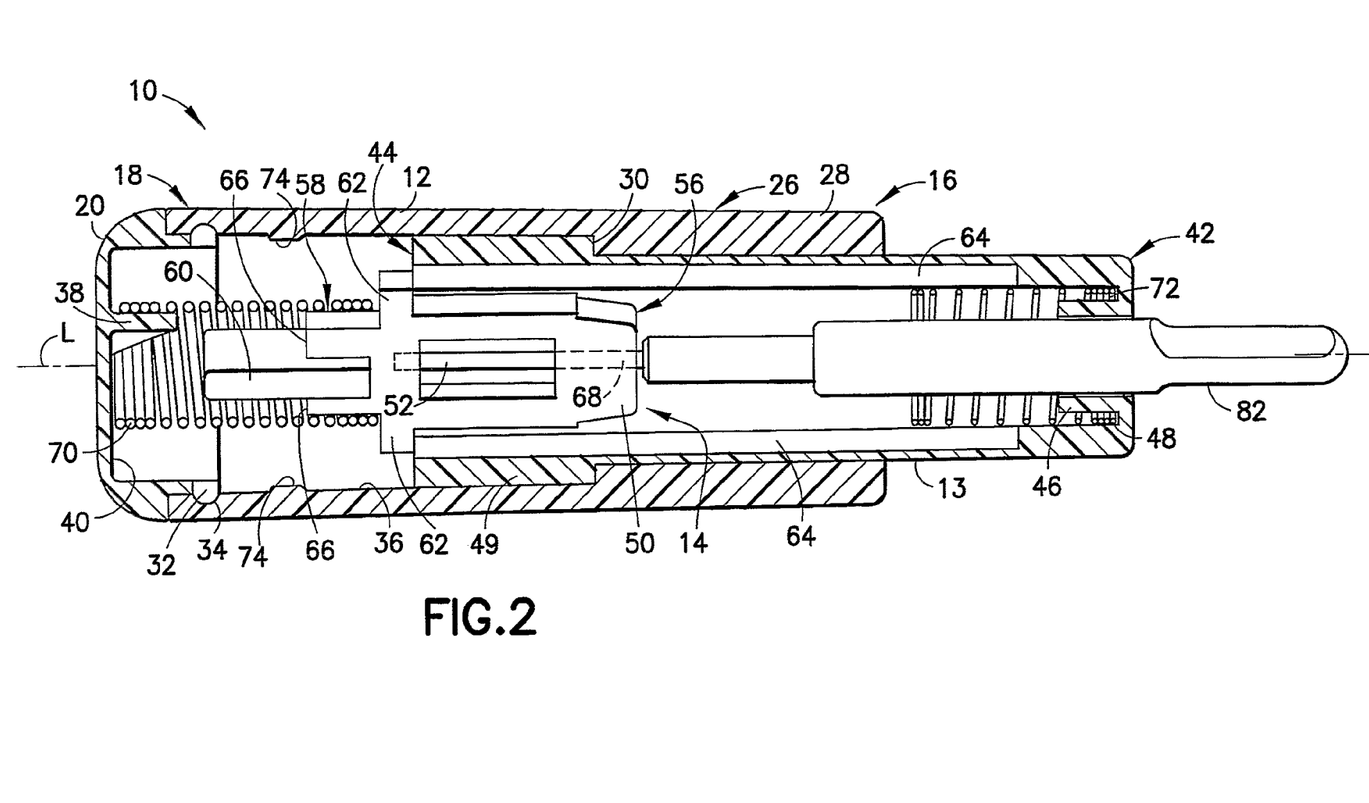
FIG. 2 is a longitudinal cross-sectional view of the medical puncturing device of FIG. 1.

As shown in FIG. 2, the skin puncturing assembly 14 is generally disposed partially within the actuator 12 and partially within the shield 13 prior to actuation of the puncturing device 10. The skin puncturing assembly 14 is axially movable relative to the actuator 12 and shield 13 once released to initiate a blood collection procedure from a patient. The skin puncturing assembly 14 generally includes an elongated carrier member 50 (hereinafter "carrier 50") and a skin puncturing element 52. The skin puncturing element 52 may be a needle, blade, or like puncturing or cutting element, and includes a sharp distal tip or end 54 for puncturing or cutting the skin of a patient from which a blood sample is to be taken. The carrier 50 may have any suitable cross section, such as a generally rectangular or polygonal-type shaped, but is sized to fit within the preferred circular or oval cross-sectional shape of the actuator 12 and shield 13 to be axially movable relative to the actuator 12 and shield 13. However, other cross sectional shapes for the carrier 50, such as circular or oval, may be used.

The carrier 50 includes a first or distal end 56 and a second or proximal end 58. The distal end 56 is generally received in the shield 13 prior to actuation of the puncturing device 10. The proximal end 58 of the carrier 50 extends toward the proximal end 18 of the actuator 12 and the inner side 40 of the end cap 20. The body of the carrier 50 is preferably formed with a centrally disposed spring guide 60, and at least one and preferably two or more radial protrusions or tabs 62. The tabs 62 are adapted to cooperate with respective longitudinal slots on grooves 64 formed or defined in the body of the shield 13. The slots or grooves 64 are formed or defined internally in the shield 13, and guide the axial distal movement of the carrier 50 relative to the shield 13 when the puncturing device 10 is actuated, as discussed further herein. Prior to actuation of the puncturing device 10, the tabs 64 are in interference engagement with the proximal end 44 of the shield 13, which maintains the positioning of the carrier 50 in the actuator 12 and shield 13.

Figure 10:
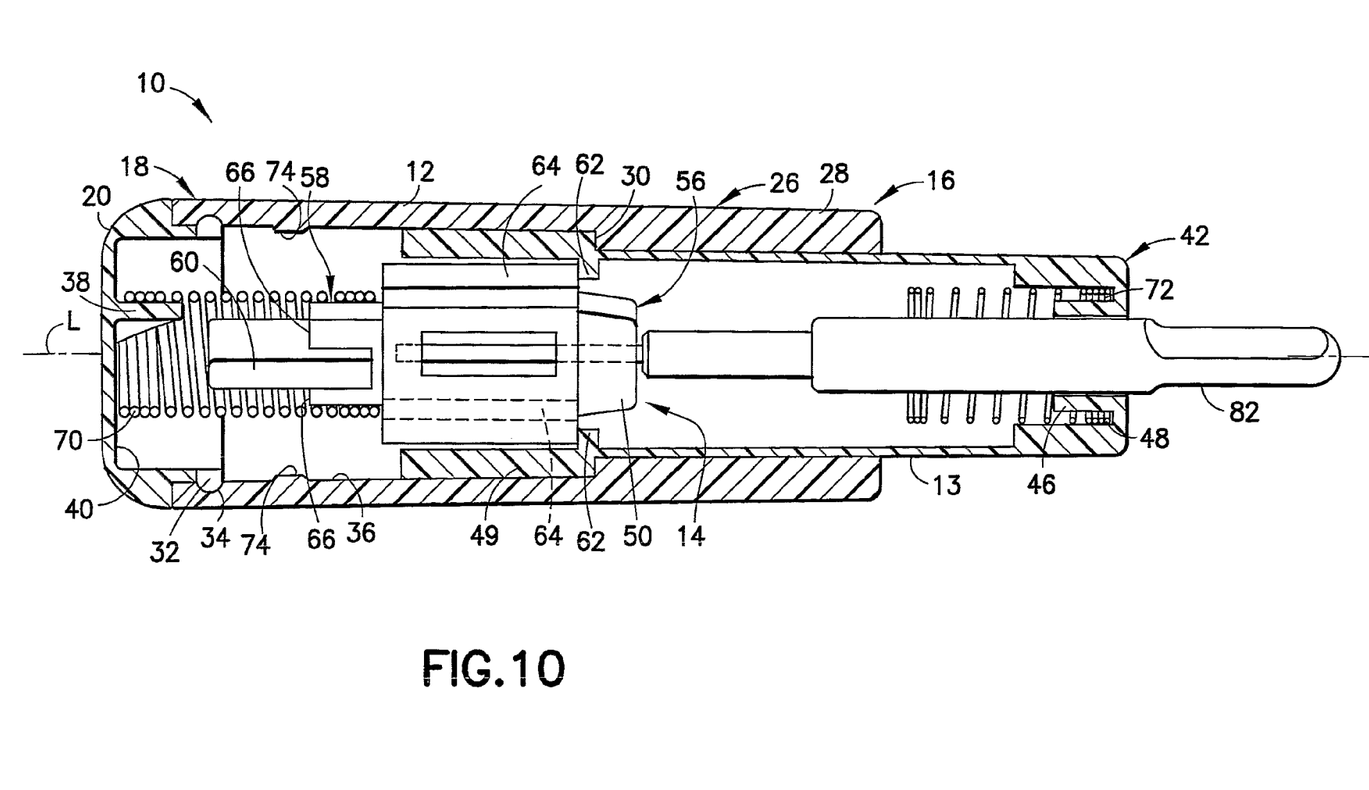
FIG. 10 is a longitudinal cross-sectional view of an alternative embodiment of the medical puncturing device of the present invention.
Figure 11A:
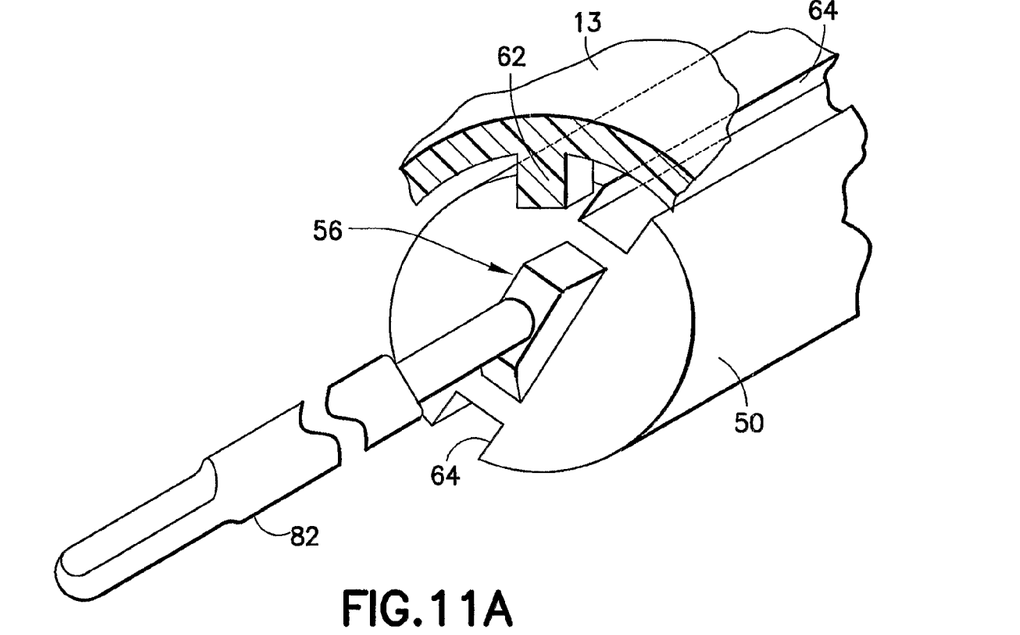
FIG. 11A is a perspective proximal end view of a skin puncturing assembly of the medical puncturing device of FIG. 10, showing interference engagement between a carrier of the skin puncturing assembly, used to support the skin puncturing element, and the shield, for maintaining the skin puncturing assembly in a retracted position within the shield.
Figure 11B:
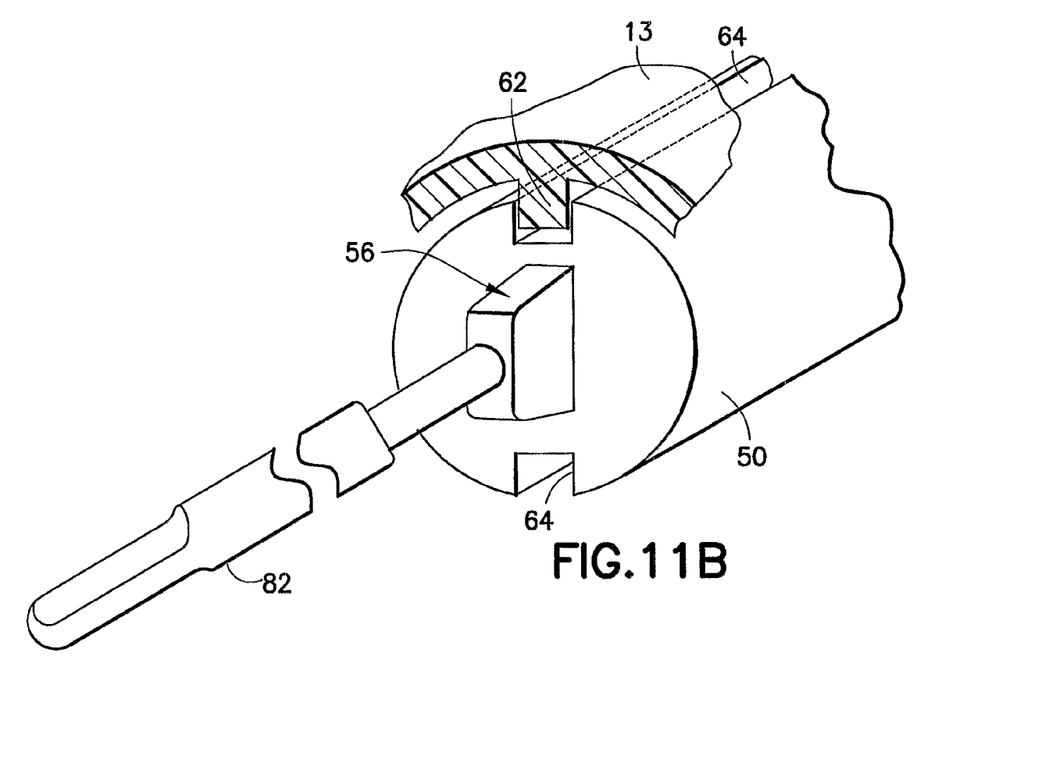
FIG. 11B is a perspective proximal end view of the skin puncturing assembly shown FIG. 11A, showing the carrier rotated to a position out of interference engagement with the shield, allowing the skin puncturing assembly to move distally in the shield.
Figure 12A:
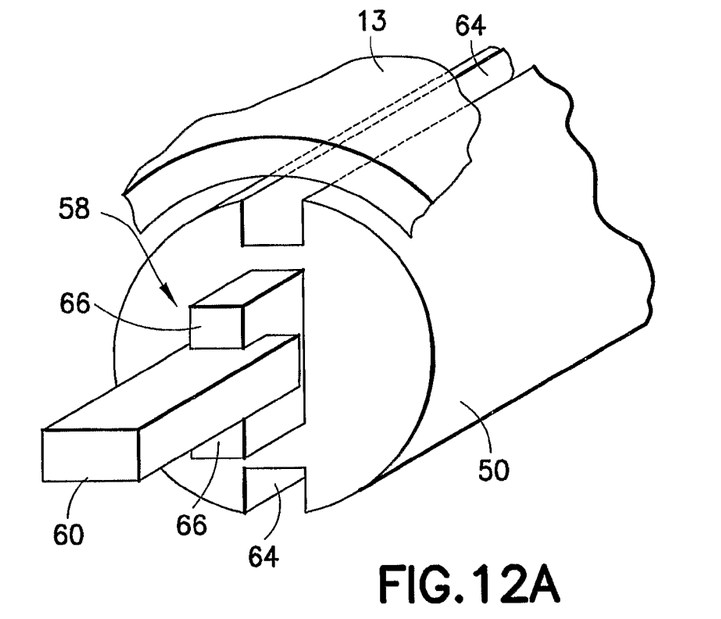
FIG. 12A is a perspective distal end view of the skin puncturing assembly shown in FIGS. 11A and 11B, showing the distal position of the skin puncturing assembly, when the skin puncturing assembly is held in the retracted position within the shield.
Figure 12B:
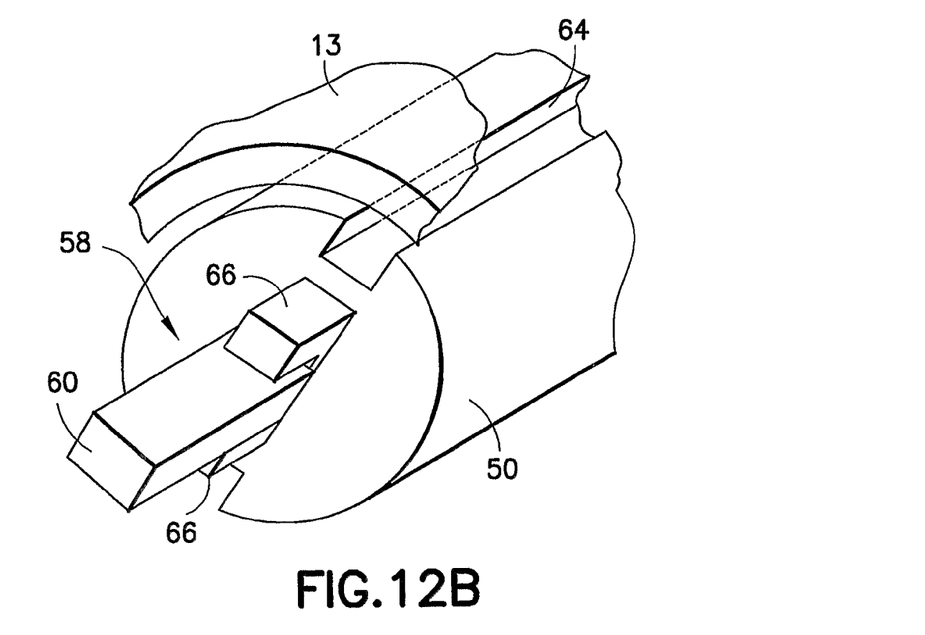
FIG. 12B is a perspective distal end view of the skin puncturing assembly shown in FIG. 12A, showing the distal position of the skin puncturing assembly, when the skin puncturing assembly is rotated or moved to a position allowing the skin puncturing assembly to move distally within the shield.

Alternatively, as shown in FIGS. 10-12, the locations for the tabs 62 and slots 64 may be reversed, with the tabs 62 extending radially inward to engage the carrier 50 and the slots 64 formed longitudinally in the body of the carrier 50. This configuration for the tabs 62 and slots 64 is discussed in further detail herein with reference to FIGS. 10-12.

Generally, actuation of the puncturing device 10 occurs automatically when the tabs 62 are aligned with the slots 64 in the shield (or vice versa). To align the tabs 62 with the slots 65, the body of the carrier 50 defines proximal cam surfaces or edges 66, which are engaged by the release elements extending from the end cap 20 (or actuator 12). In particular, during the actuation of the puncturing device 10, the arcuate-shaped cam surfaces or edges 39 of the release elements 38, or a distally extending portion of the actuator, are fixed relative to the actuator and engage the cam surfaces or edges 66, which cause the carrier 50 to rotate about a central longitudinal axis L of the puncturing device 10. The rotation of the carrier 50 aligns the tabs 62 with the slots 64, enabling the carrier 50 to move distally in the shield 13, as discussed further herein.

The skin puncturing element 52 generally extends from the distal end 56 of the carrier 50 and is received within a central bore 68 formed centrally within the body of the carrier 50. The skin puncturing element 52 may be secured in the central bore 68 by a medical-grade adhesive or by other techniques customary in the medical field. The skin puncturing element 52 is depicted in the Figures of this disclosure as a needle. However, as indicated previously, the skin puncturing element 52 is not necessarily limited to a needle or other puncturing-type element, but could also be a blade for causing an incision-type wound in the skin of a patient when the puncturing device 10 is actuated.

The puncturing device 10 further includes a drive or firing spring 70 disposed in the actuator 12 and received at least partially about the carrier 50. More particularly, the drive spring 70 is received about the proximal end 58 of the carrier 50 and about the spring guide 60 extending from the proximal end 58 of the carrier 50. The drive spring 70 may be connected to the proximal end 58 of the carrier 50 by frictional engagement therewith, or connected to the proximal end 58 by other means customary in the medical field, such as with a medical-grade adhesive or by a mechanical fastener or like element.

Figure 8:
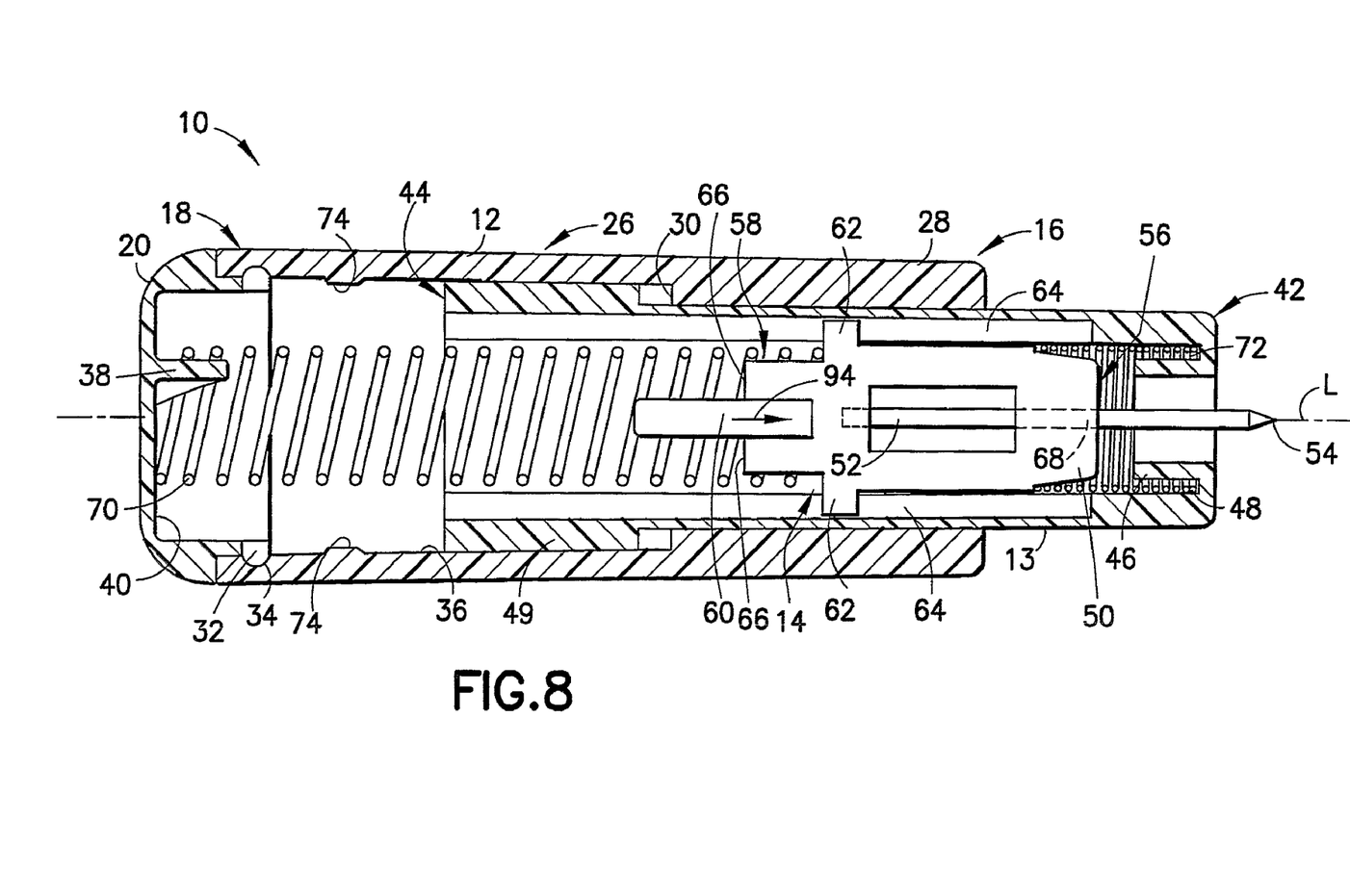
FIG. 8 is a longitudinal cross-sectional view of the medical puncturing device of FIG. 1, showing the medical puncturing device immediately after actuation with a skin piercing element of the medical puncturing device exposed momentarily to pierce the skin of a patient.

The drive spring 70, when actuated or released, provides the force necessary to move the skin puncturing assembly 14 distally within the actuator 12 and through the shield 13. The drive spring 70 further provides the force necessary to puncture the skin of a patient when the puncturing device 10 is used in a blood-drawing or collecting procedure. More particularly, the drive spring 70 is adapted to move the carrier 50 within the actuator 12 from the retracted position shown in FIG. 2 to an extended or puncturing position as shown in FIG. 8 discussed herein. In the retracted position of the carrier 50, the sharp distal tip 54 of the skin puncturing element 52 is contained or encompassed within the actuator 12 and, more particularly, the shield 13. In the extended or puncturing position, the skin puncturing element 52 extends outward from the distal end 42 of the shield 13, and the sharp distal tip 54 of the skin puncturing element 52 is exposed for causing a puncturing or incision-type wound in the skin of a patient.

The drive spring 70 generally extends between the proximal end 58 of the carrier 50 and the inner side 40 of the end cap 20. As shown in FIG. 2, the drive spring 70 is preferably held in a partially compressed state within the actuator 12 prior to actuation of the puncturing device 10. The drive spring 70 is held in the compressed state by the misalignment of the tabs 62 on the carrier 50 with the slots 64 in the shield 13 (or vice versa), which results in an interference engagement between the carrier 50 and shield 13. The drive spring 70 is generally compressed between the proximal end 58 of the carrier 50 and the inner side 40 of the end cap 20 and, further, desirably between the tabs 62 on the carrier 50 and the inner side 40 of the end cap 20.

The puncturing device 10 may further include a return or retraction spring 72 disposed in the shield 12 to provide the force necessary to generally return the skin puncturing assembly 14 to a static condition within the actuator 12 and shield 13 after the puncturing device 10 is actuated by a user. More particularly, the retraction spring 72 provides the force necessary to return the carrier 50 to a position within the actuator 12 and shield 13 wherein the skin puncturing element 52 and sharp distal tip 54 thereof are substantially contained or encompassed within the shield 13. The retraction spring 72 is optional in the puncturing device 10, and the tension force of the drive spring 70 may be used to return the carrier 50 to a position wherein the shield 13 encompasses the sharp distal tip 54 of the skin puncturing assembly 14. The retraction spring 72 is generally seated in the pocket 48 formed by the internally-extending portion 46 of the shield 13. The retraction spring 72 generally acts against the distal end 56 of the carrier 50 as the drive spring 70 biases the carrier 50 toward the distal end 16 of the actuator 12 and, further, the distal end 42 of the shield 13 when the puncturing device 10 is actuated by a user. The retraction spring 72 is in a generally uncompressed state prior to actuation of the puncturing device 10 as shown in FIG. 2. The retraction spring 72 may be secured in the pocket 48 formed by the internally-extending portion 46 of the shield 13 by a suitable medical-grade adhesive or by equivalent mechanical means, if desired. Otherwise, a frictional engagement between the retraction spring 72 and the pocket 48 is all that is necessary to secure the retraction spring 72 to the shield 13 in accordance with an embodiment of the present invention. The proximal movement of the shield 13 relative to the actuator 12 may be limited by a circumferentially-extending detent or tab 74, formed on the internal surface 36 of the actuator 12. The skin puncturing assembly 14 may further include a protective tip guard 82 connected to the carrier 50. The tip guard 82 may be formed integrally with the body of the carrier 50, but include a notched connection (not shown) with the distal end 56 of the carrier 50. If a notched connection is provided between the tip guard 82 and the carrier 50, this connection enables the user of the puncturing device 10 to simply and easily break the integral connection between the tip guard 82 and carrier 50, and remove the tip guard 82 prior to actuating the puncturing device 10.

The tip guard 82 defines a central bore 84, which receives the skin puncturing element 82 and, further, the sharp distal tip 54 thereof. The tip guard 82 preferably extends outward from the distal end 16 of the actuator 12 and distal end 42 of the shield 13 as shown in FIGS. 1 and 2. The tip guard 82 ensures that the sharp distal tip 54 of the puncturing element 52 remains sterile before use and, further, protects the user against accidental puncture wounds that could be caused by inadvertent or premature actuation of the puncturing device 10. The tip guard 82 may be removed by simply pulling on the tip guard 82 or, if a notched connection is provided with the body of the carrier 50, by moving the tip guard 82 in a side-to-side manner in the open distal end 42 of the shield 13 until the notched connection with the carrier 50 breaks, as is well-known in the art.

The assembly of the puncturing device 10 is a straightforward process. The actuator 12 is provided first and, as discussed previously, includes open distal and proximal ends 16, 18. Next, the shield 13, preferably containing the retraction spring 72, may be inserted into the open proximal end 18 of the actuator 12, such that the distal end 42 of the shield 13 extends outward from the distal end 16 of the actuator 12. The engagement of the proximal portion 49 on the shield 13 with the internal edge 30 defined by the distal portion 28 of the actuator 12 limits the axial distal movement of the shield 13 relative to the actuator 12. Once the shield 13 is in place, the skin puncturing assembly 14 may be inserted into the open proximal end 18 of the actuator 12. The skin puncturing assembly 14 is generally inserted into the actuator 12 so that the tabs 62 are misaligned with the slots 64.

With the skin puncturing assembly 14 in place within the actuator 12 and shield 13, the drive spring 70 may be inserted into the actuator 12 through the open proximal end 18 of the actuator 12. The drive spring 70 is received about the proximal end 58 of the carrier 50 and the spring guide 60 extending from the proximal end 58 of the carrier 50. The actuator proximal end 18 is then closed with the end cap 20. The drive spring 70 generally encompasses the release elements 38 on the inner side 40 of the end cap 20. The drive spring 70 is generally placed in a slightly compressed, pre-actuated state within the actuator 12 by affixing the end cap 20 to the actuator proximal end 18. The end cap 20 is secured to the actuator 12 by engagement of the detent 32 on the end cap 20 with the recess 34 in the actuator 12. The assembled puncturing device 10 is now ready for use.

Figure 6:
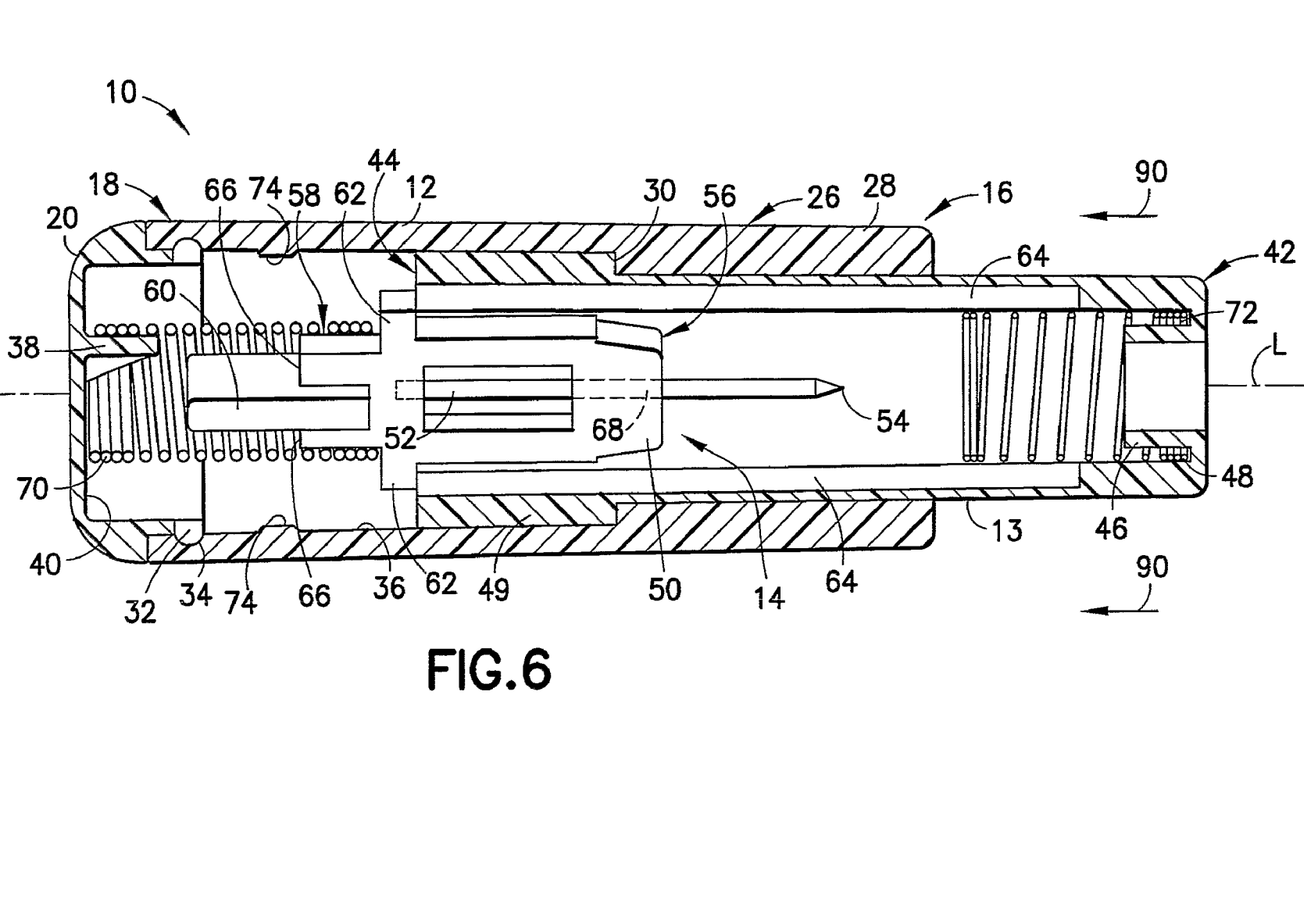
FIG. 6 is a longitudinal cross-sectional view of the medical puncturing device of FIG. 1, showing the medical puncturing device prior to actuation and with the tip guard removed.
Figure 7:
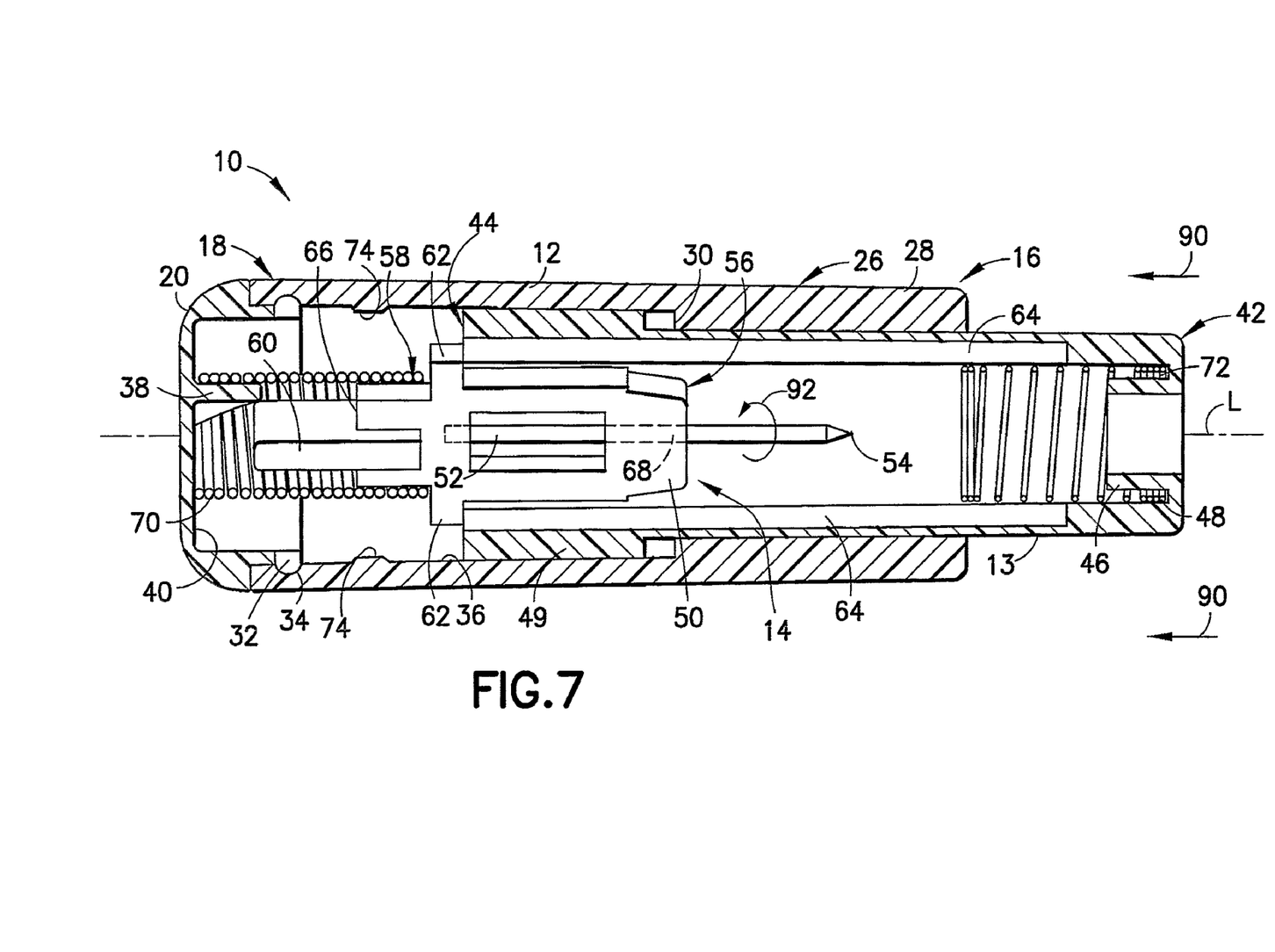
FIG. 7 is a longitudinal cross-sectional view of the medical puncturing device of FIG. 1, showing the medical puncturing device during actuation and the direction of forces applied to actuate the medical puncturing device.

Referring to FIGS. 6-9, the general sequence of actuation for the puncturing device 10 will now be discussed. FIG. 6 shows the puncturing device 10 in a pre-actuated state in a similar manner to FIG. 2 discussed previously but with the tip guard 82 removed. In the pre-actuated state, the drive spring 70 is held in a partially compressed state between the end cap 20 and the proximal end 58 of the carrier 50 by the misalignment of the tabs 62 on the carrier 50 with the slots 64 in the shield 13, which causes the tabs 62 to be in interference engagement with the proximal end 44 of the shield 13. Additionally, in the pre-actuated state, the retraction spring 72 is disposed in the pocket 24 formed at the distal end 42 of the shield 13 and is in an uncompressed state. To actuate the puncturing device 10, the user grasps the actuator 12 between the thumb and forefinger, preferably with the thumb and forefinger substantially engaging the finger pads 22 on the external surface 26 of the actuator 12. The user then places the distal end 42 of the shield 13 in contact with the body part where a blood sample is to be taken. The user exerts a distally-directed force on the actuator 12, which causes the shield 13 to move proximally into the actuator 12 (i.e., relative movement between the actuator 12 and shield 13) in the direction of arrows 90 in FIG. 6. This simultaneously causes the shield 13 to move the carrier 50 proximally toward the inner side 40 of the end cap 20 because of the interference engagement between the tabs 62 and the proximal end 44 of the shield 13. As the carrier 50 and shield 13 move proximally in the actuator 12, the drive spring 70 is further compressed between the proximal end 58 of the carrier 50 and the inner side 40 of the end cap 20 and, more preferably, between the tabs 62 and the inner side 40 of the end cap 20, increasing the stored or potential energy in the drive spring 70.

As the proximal end 58 of the carrier 50 approaches the release elements 38, the release elements 38 begin to engage or coact with the proximal end 58 of the carrier 50. In particular, the cam surfaces or edges 39 on the release elements 38 contact and coact with the proximal cam surfaces or edges 66 on the carrier 50, causing the carrier 50 to rotate about the central longitudinal axis L of the puncturing device 10. The shape of the cam surfaces or edges 39 on the release elements 38 is generally configured to have an angled surface so that contact therewith causes the carrier 50 to rotate sufficiently to allow the tabs 62 on the carrier 50 to align with the slots 64 in the shield 13. The rotational movement of the carrier 50 caused by the release elements 38 is identified with arrow 92 in FIG. 7.

Once the tabs 62 are aligned with the slots 64, the tabs 62 are no longer in interference engagement with the proximal end 44 of the shield 13 and the carrier 50 is free to move distally into the actuator 12 and shield 13. Additionally, the drive spring 70 is also released of compression between the carrier 50 and end cap 20, and automatically biases or drives the carrier 50 toward the distal end 42 of the shield 13. The engagement of the tabs 62 in the slots 64 guides the movement of the carrier 50 in the shield 13.

FIG. 8 shows the released movement of the carrier 50 in the actuator 12 and shield 13. The carrier 50 of the skin puncturing assembly 14 is released from the retracted position or configuration shown in FIG. 6 and moves to a puncturing position or configuration shown in FIG. 8, wherein the skin puncturing element 52 extends outward from the distal end 42 of the shield 13, and the sharp distal tip 54 of the puncturing element 52 is fully exposed for piercing or cutting the skin of a patient. The carrier 50 of the skin puncturing assembly 14 is released by axially displacing the shield 13 into the actuator 12 (i.e., relative movement between these elements). The direction of movement of the carrier 50 in the actuator 12 and shield 13 upon actuation of the puncturing device 10 is identified by arrow 94 in FIG. 8. In the puncturing position or configuration shown in FIG. 8, the skin puncturing element 52 of the skin puncturing assembly 14 reaches its maximum extension from the distal end 42 of the shield 13 and is driven under the force of the drive spring 70 into the skin of the patient (not shown). The drive spring 70 preferably has sufficient stored or potential energy to cause the sharp distal tip 54 of the skin puncturing element 52 to pierce the skin of a person or animal once released of compression between the inner side 40 of the end cap 20 and the carrier 50.

Figure 9:
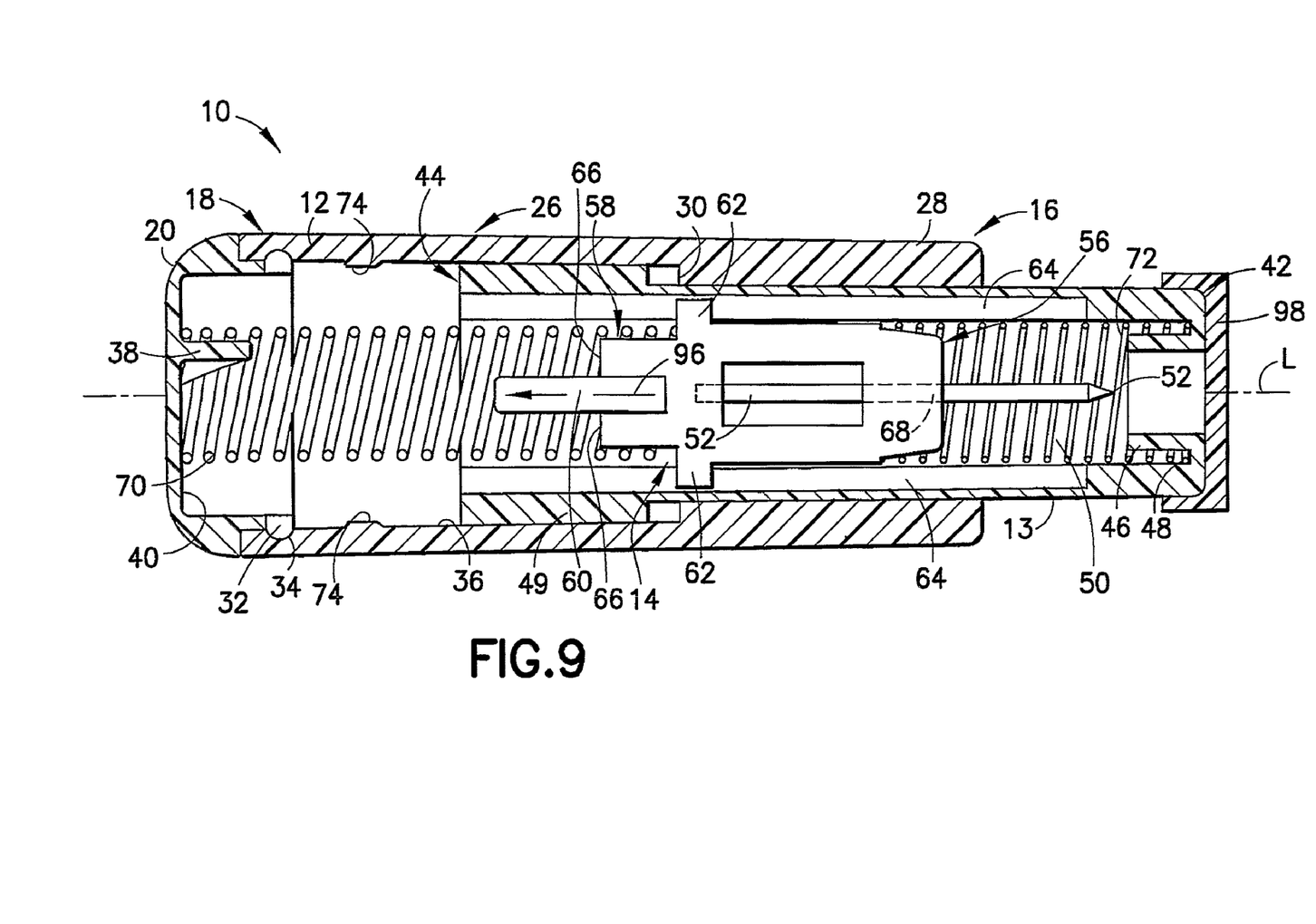
FIG. 9 is a longitudinal cross-sectional view of the medical puncturing device of FIG. 1, showing the device after actuation with the skin piercing element returned to a position substantially encompassed by the shield.

FIG. 9 shows the ultimate disposition of the carrier 50 within the actuator 12 and shield 13 after the puncturing device 10 has been actuated. As shown in FIG. 8, as the carrier 50 reaches the puncturing position wherein the sharp distal tip 54 of the skin puncturing element 52 is fully exposed, the retraction spring 72 is compressed at least partially between the distal end 56 of the carrier 50 and the distal end 42 of the shield 13. The retraction spring 72 is thereby compressed in the pocket 48. The compression of the retraction spring 72 provides a return or retraction force that acts on the carrier 50 to move the carrier 50 in a return or retraction direction in the actuator 12, as identified with arrow 96 in FIG. 9, which returns or retracts the skin puncturing element 52 and the sharp distal tip 54 thereof fully into the actuator 12 and shield 13. The retraction spring 72 thereafter prevents the reemergence of the skin puncturing element 52 from the shield 13. As indicated previously, the tension force of the drive spring 70 may be sufficient to return or retract the carrier 50 within the actuator 12 and shield 13. Thus, the retraction spring 72 may be omitted in the puncturing device 10.

If desired, a protector cap 98 may be provided to enclose the distal end 42 of the shield 13 to further ensure that the skin puncturing element 52 will not extend outward from the shield 13, particularly after the puncturing device 10 has been actuated. The protector cap 98 is removable from the shield 13 and may generally take the place of the tip guard 82 discussed previously. Thus, the removable protector cap 98 may be provided on the distal end 42 of the shield 13 prior to actuation of the puncturing device 10 and reapplied or replaced thereon after the puncturing device 10 has been actuated.

As discussed previously, the locations for the tabs 62 and slots 64 may be reversed, as generally illustrated in an alternative embodiment of the puncturing device 10 shown FIGS. 10-12. Thus, the tabs 62 may extend radially inward toward the central longitudinal axis L of the puncturing device 10, and the slots 64 may be formed in the body of the carrier 50, longitudinally on the body of the carrier 50. In this embodiment of the puncturing device 10, the tabs 62 extend inward to engage the body of the carrier 50, preferably at the distal end 56 of the carrier 50, to maintain the carrier 50 of the skin puncturing assembly 14 in the retracted position until actuation of the puncturing device 10. The tabs 62 engage the distal end 56 of the carrier 50 and, more particularly, a distal end edge formed by the distal end 56 of the carrier 50. The tabs 62 engage the distal end 56 of the carrier 50 between the longitudinal slots 64 in the body of the carrier 50 (i.e., opposing sides of the carrier 50) in the retracted position of the carrier 50. The engagement of the tabs 62 with the distal end 56 of the carrier 50 maintains the carrier 50 in the retracted position within the actuator 12 and shield 13 until actuation of the puncturing device 10, which occurs when the carrier 50 is rotated or moved to a position wherein the tabs 62 engage or coincide with the slots 62 in the body of the carrier 50. The tabs 62 may be formed as part of, and extend inward from, the proximal portion 49 of the shield 13, as shown in FIG. 10.

Other than the reversed locations for the tabs 62 and slots 64, the embodiment of the puncturing device 10 shown in FIGS. 10-12 is substantially identical to the puncturing device 10 illustrated in FIGS. 1-9 discussed previously, and is actuated in generally the same manner as discussed previously. Generally, relative movement between the shield 13 and actuator 12 causes the release elements 38 to engage the carrier 50 and rotates the carrier 50 about the central longitudinal axis L of the puncturing device 10. Such rotation causes the tabs 62 extending from the shield 13 to align with the slots 64 in the body of the carrier 50 and disengage from the distal end 56 of the carrier 50, which allows the skin puncturing assembly 14 to move axially within the actuator 12 and shield 13, and execute a skin puncturing or cutting movement.

While the present invention was described with reference to preferred embodiments of the medical puncturing device, those skilled in the art may make modifications and alterations to the present invention without departing from the scope and spirit of the invention. Accordingly, the above detailed description is intended to be illustrative rather than restrictive. The invention is defined by the appended claims, and all changes to the invention that fall within the meaning and range of equivalency of the claims are to be embraced within their scope.

What is claimed:

1. A medical puncturing device, comprising:
   an actuator having at least one rigid release element extending therefrom, the actuator including gripping surfaces on opposing sides thereof for grasping the actuator between the fingertips of a user;

a shield, the shield and the actuator movably associated with each other; and a skin puncturing assembly disposed at least partially within the shield, the skin puncturing assembly comprising a carrier and a skin puncturing element mounted to the carrier, a distal end of the skin puncturing element adapted for puncturing the skin of a patient, the carrier movable from a first position to a second position;

wherein the at least one rigid release element is configured such that relative movement between the actuator and shield causes the at least one rigid release element to engage the carrier and align at least one tab provided on one of the carrier and shield with at least one slot formed in the other of the carrier and shield, enabling the carrier to move from the first position to the second position;

wherein a force applied to the distal end of the shield causes the shield to move proximally relative to the actuator to cause the rigid release element to engage with the carrier about a central axis of the puncturing device enabling the carrier to move from the first position to the second position; and wherein at least one of the rigid release element or the carrier comprises a cam surface and the other of the rigid release element and the carrier comprises a corresponding contact surface edge, the cam surface or the corresponding contact surface edge is fixed relative to the actuator during actuation and has a shape configured to rotate the carrier and wherein relative movement between the actuator and the shield causes the cam surface and the corresponding contact surface edge to contact and the shape of the cam surface or the corresponding contact surface edge causes rotation of the carrier about a central axis of the puncturing device to align the at least one tab with the at least one slot.

2. The medical puncturing device of claim 1, wherein:
when in the first position, the distal end of the skin puncturing element is disposed within the shield; and
when in the second position, the distal end of the skin puncturing element is exposed from the distal end of the shield to puncture the skin of the patient.

3. The medical puncturing device of claim 1, wherein the alignment of the at least one tab with the at least one slot is accomplished by engagement of the at least one rigid release element with the carrier, thereby rotating the carrier about a longitudinal axis of the medical puncturing device.

4. The medical puncturing device of claim 1, wherein the at least one tab is provided on the carrier and the at least one slot is formed in the shield, and wherein the at least one tab is in interference engagement with the shield to maintain the carrier in the first position, until the relative movement between the actuator and shield causes the at least one rigid release element to engage the carrier and align the at least one tab with the at least one slot.

5. The medical puncturing device of claim 1, wherein the at least one tab extends from the shield and the at least one slot is formed in the carrier, and wherein the at least one tab is in interference engagement with the carrier to maintain the carrier in the first position, until the relative movement between the actuator and shield causes the at least one rigid release element to engage the carrier and align the at least one slot with the at least one tab.

6. The medical puncturing device of claim 1, wherein the at least one rigid release element has a surface adapted to rotate the carrier about a longitudinal axis of the medical puncturing device, upon the relative movement between the actuator and shield.

7. The medical puncturing device of claim 1, further comprising a drive spring acting between the carrier and the actuator, the drive spring adapted to move the carrier from the first position to the second position upon alignment of the at least one tab with the at least one slot.

8. The medical puncturing device of claim 7, further comprising a retraction spring disposed within the shield at the shield distal end, the retraction spring adapted to return the carrier to a position wherein the shield encompasses the skin puncturing element after the carrier reaches the second position.

9. The medical puncturing device of claim 1, further comprising a removable protector cap on the distal end of the shield.

10. The medical puncturing device of claim 1, wherein the actuator extends axially along an external surface of the shield along a longitudinal axis of the medical puncturing device and a proximal end of the shield is disposed within the actuator.

11. The medical puncturing device of claim 1, wherein the cam surface has an angled surface so that contact therewith causes the carrier to rotate with respect to this angled surface.

12. A medical puncturing device, comprising:
an actuator;
a shield, the shield and the actuator movably associated with each other; and
a skin puncturing assembly disposed at least partially within the shield, the skin puncturing assembly comprising a carrier and a skin puncturing element mounted to the carrier, the carrier movable from a first position to a second position;
wherein the actuator extends axially over an external surface of the shield along a longitudinal axis of the medical puncturing device, a proximal end of the shield being disposed within the actuator, wherein the actuator comprises surfaces on opposing sides thereof for gripping the actuator between the finger tips of a user,
wherein, when the carrier is in the first position, the shield has a shield interference surface engageable with a carrier interference surface of the carrier; and
wherein the carrier is capable of rotation when a force is applied to the actuator, causing a portion of the carrier to engage a distally extending portion of the actuator and wherein at least a portion of the distally extending portion is fixed relative to the actuator during actuation and the rotation enables disengagement of the shield interference surface from the carrier interference surface, thereby causing the carrier to move from the first position to the second position.

13. The medical puncturing device of claim 12:
wherein the skin puncturing element includes a distal end adapted for puncturing the skin of a patient; and
wherein, when in the first position, the distal end of the skin puncturing element is disposed within the shield having a distal end, and when in the second position, the distal end of the skin puncturing element is exposed from the distal end of the shield to puncture the skin of the patient.

14. The medical puncturing device of claim 13, wherein the carrier is rotated about a longitudinal axis of the medical puncturing device.

15. The medical puncturing device of claim 14, wherein the carrier is rotated about upon relative movement between the actuator and shield.

16. A method of assembling a medical puncturing device, comprising:
  providing an actuator having an open proximal end and an open distal end;
  inserting a shield into the actuator proximal end, a distal end of the shield extending outward from the actuator distal end;
  inserting a skin puncturing assembly into the actuator proximal end, the skin puncturing assembly comprising a movable carrier and a skin puncturing element mounted to the carrier, the skin puncturing element having a distal end adapted for puncturing the skin of a patient; and
  wherein the skin puncturing assembly is inserted into the actuator proximal end such that:
  the shield has a shield interference surface engageable with a carrier interference surface of the carrier, when the carrier is in a first position; and
  the carrier is capable of rotation when a force is applied to the actuator causing a portion of the carrier to engage a distally extending portion of the actuator and wherein at least of portion of the distally extending portion is fixed with relative to the actuator during actuation and the rotation enables disengagement of the shield interference surface from the carrier interference surface, thereby causing the carrier to move from the first position to a second position;
  wherein the actuator extends axially over an external surface of the shield along a longitudinal axis of the medical puncturing device, a proximal end of the shield being disposed within the actuator, wherein the actuator comprises surfaces on opposing sides thereof for gripping the actuator between the fingertips of a user.

17. A method of actuating a medical puncturing device comprising:
  providing the medical puncturing device comprising an actuator, a shield, and a skin puncturing assembly disposed at least partially within the shield, the skin puncturing assembly comprising a movable carrier and a skin puncturing element mounted to the carrier, the skin puncturing element having a distal end adapted for puncturing the skin of a patient, the actuator extending axially over an external surface of the shield along a longitudinal axis of the medical puncturing device, a proximal end of the shield being disposed within the actuator, wherein the actuator comprises surfaces on opposing sides thereof for gripping the actuator between the fingertips of a user, the actuator and shield movably associated with each other;
  wherein a force applied to a distal end of the shield causes the shield to move proximally relative to the actuator such that a distally extending portion of the actuator engages the carrier wherein at least a portion of the distally extending portion is fixed relative to the actuator during actuation to rotate the carrier from an interference engagement with the shield to a position allowing the skin puncturing assembly to move axially within the shield to a position exposing the distal end of the skin puncturing element for puncturing the skin of the patient.

18. The method of claim 17, wherein the distally extending portion of the actuator includes at least one rigid release element extending therefrom, and at least one of the rigid release element or the carrier comprises a cam surface and the other of the rigid release element or the carrier comprises a corresponding contact surface edge, the cam surface or the corresponding contact surface edge having a shape configured to rotate the carrier and wherein relative movement between the actuator and the shield causes the cam surface and the corresponding contact surface edge to contact and the shape of the cam surface or the corresponding contact surface edge causes rotation of the carrier about a central axis of the puncturing device to rotate the carrier from the interference engagement with the shield.

19. The method of claim 18, wherein the cam surface has an angled surface so that contact therewith causes the carrier to rotate with respect to this angled surface.

20. A method of actuating a medical puncturing device comprising:
  providing the medical puncturing device comprising an actuator, a shield, and a skin puncturing assembly disposed at least partially within the shield, the skin puncturing assembly comprising a movable carrier and a skin puncturing element mounted to the carrier, the skin puncturing element having a distal end adapted for puncturing the skin of a patient, the actuator extending axially over an external surface of the shield along a longitudinal axis of the medical puncturing device, a proximal end of the shield being disposed within the actuator, wherein the actuator comprises surfaces on opposing sides thereof for gripping the actuator between the fingertips of a user and the actuator and shield movably associated with each other;
  wherein a force applied to a distal end of the shield causes the shield to move proximally relative to the actuator such that a distally extending portion of the actuator engages the carrier wherein at least a portion of the distally extending portion is fixed relative to the actuator during actuation to rotate the carrier from an interference engagement with the shield to a position allowing the skin puncturing assembly to move axially within the shield to a position exposing the distal end of the skin puncturing element for puncturing the skin of the patient and causing relative axial movement between the actuator and shield, such that the actuator rotates a rigid release element associated with the carrier to a position allowing the carrier to move axially within the shield to a position exposing the distal end of the skin puncturing element for puncturing the skin of the patient.

* * * * *